United States Patent [19]

Blum et al.

[11] 4,267,108

[45] May 12, 1981

[54] HYDROXYALKANE DIPHOSPHONIC ACIDS

[75] Inventors: Helmut Blum, Düsseldorf; Hans-Ulrich Hempel, Overath; Karl-Heinz Worms, Düsseldorf, all of Fed. Rep. of Germany

[73] Assignee: Henkel Kommanditgesellschaft auf Aktien, Düsseldorf-Holthausen, Fed. Rep. of Germany

[21] Appl. No.: 944,603

[22] Filed: Sep. 21, 1978

[30] Foreign Application Priority Data

Oct. 7, 1977 [DE] Fed. Rep. of Germany ....... 2745083

[51] Int. Cl.³ ..................... C07D 207/12; C07F 9/02
[52] U.S. Cl. ..................... 260/326.61; 260/502.5; 424/200; 424/211
[58] Field of Search ..................... 260/326.61, 502.5

[56] References Cited

U.S. PATENT DOCUMENTS

| | | | |
|---|---|---|---|
| 3,925,453 | 12/1975 | Clarke | 260/326.61 |
| 3,941,772 | 3/1976 | Ploger et al. | 260/326.61 |

FOREIGN PATENT DOCUMENTS

| | | | |
|---|---|---|---|
| 1082235 | 9/1958 | Fed. Rep. of Germany | 260/502.5 |
| 981252 | 1/1965 | United Kingdom . | |
| 1435885 | 5/1976 | United Kingdom . | |

OTHER PUBLICATIONS

Ploger et al., Z anorg. allg. Chem., 389, pp. 119–128, (1972).
Kabachnik et al., Chem. Abst, 69, 5682h, (1968).
Henkel C. A., 59, 11566 C & D (1963), Abstract of Belgian Patents 619,619 and 619,620, issued 3/7/71.

*Primary Examiner*—Donald G. Daus
*Assistant Examiner*—W. B. Springer
*Attorney, Agent, or Firm*—Hammond & Littell, Weissenberger and Muserlian

[57] ABSTRACT

Hydroxyalkane diphosphonic acids having the formula

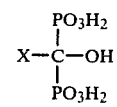

wherein X is a member selected from the group consisting of

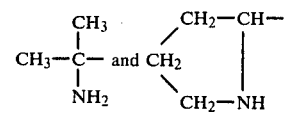

and their water-soluble salts; as well as the process of preparing the same.

The compounds are excellent sequestering agents, especially for alkaline earth and earth metal ions. They are stabilizers for percompounds and are useful in the delaying of the setting times for gypsum. In addition, the compounds are useful in cosmetic preparations, such as toothpastes and mouthwashes where they prevent formation of tartar and plaque and are useful in therapy in the treatment of diseases related to the abnormal deposition or dissolution of difficultly soluble calcium salts in the animal body.

3 Claims, No Drawings

HYDROXYALKANE DIPHOSPHONIC ACIDS

BACKGROUND OF THE INVENTION

Aminoalkane diphosphonic acids and their salts, possibly also containing a hydroxy group, are gaining increasing interest in recent times because of their good efficiency as complex formers, in particular also in sub-stoichiometric quantities (threshold amounts); as well as in pharmaceutical products.

Compounds of this kind are, for example, the 3-aminoalkane-1,1-diphosphonic acids such as 1,3-diaminopropane-1,1-diphosphonic acid or 3-amino-1-hydroxypropane-1,1-diphosphonic acid. Despite their good effectiveness, these known compounds are not satisfactory in all properties. For example, they have only a moderate threshold effect at low dosages. Besides, in certain pH ranges, relatively poorly soluble alkaline earth complexes occur in part.

OBJECTS OF THE INVENTION

An object of the present invention is the development of an hydroxyalkane diphosphonic compound selected from the group consisting of (A) acids having the formula $$X-\underset{PO_3H_2}{\overset{PO_3H_2}{\underset{|}{\overset{|}{C}}}}-OH$$

wherein X is a member selected from the group consisting of

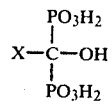 and 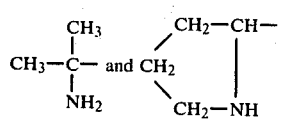

and (B) a non-toxic pharmacologically acceptable water-soluble salt thereof.

Another object of the present invention is the development of a process for the production of the above hydroxyalkane disphosphonic compound consisting of the steps of reacting an aminocarboxylic acid selected from the group consisting of 2-amino-isobutyric acid and proline with phosphorous acid and phosphorus trichloride at a temperature of from 50° C. to 140° C., where the ratio of aminocarboxylic acid to phosphorous acid to phosphorus trichloride is from 1:1:1 to 1:3:3, hydrolyzing the reaction product under acidic conditions, and recovering said hydroxyalkane diphosphonic compound.

A further object of the present invention is the development of a process for the delaying or inhibiting of the precipitation of alkaline earth metal ions from aqueous solutions by the use of stoichiometric to sub-stoichiometric amounts of the above hydroxyalkane diphosphonic compound.

These and other objects of the present invention will become more apparent as the description thereof proceeds.

DESCRIPTION OF THE INVENTION

The subject of the invention is new 1-hydroxyalkane-1,1-diphosphonic acids and the water-soluble salts thereof. The said compounds are good complex formers and exhibit additional valuable properties in applied technology. Unexpectedly, it was found that the new 1-hydroxyalkane-1,1-diphosphonic acids described hereinafter have considerably better properties than the 3-aminoalkane-1,1-diphosphonic acids of the prior art.

The new 1-hydroxyalkane-1,1-diphosphonic acids of the present invention correspond to the general formula I

where X signifies

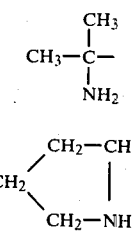

or

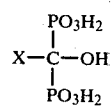

and their water-soluble salts.

More particularly, the present invention relates to an hydroxyalkane diphosphonic compound selected from the group consisting of (A) acids having the formula $$X-\underset{PO_3H_2}{\overset{PO_3H_2}{\underset{|}{\overset{|}{C}}}}-OH$$

wherein X is a member selected from the group consisting of

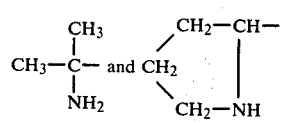

and (B) a non-toxic pharmacologically acceptable water-soluble salt thereof.

In addition, the invention also relates to a process for the production of the above hydroxyalkane diphosphonic compound consisting of the steps of reacting an aminocarboxylic acid selected from the group consisting of 2-amino-isobutyric acid and proline with phosphorous acid and phosphorus trichloride at a temperature of from 50° C. to 140° C., where the ratio of aminocarboxylic acid to phosphorous acid to phosphorus trichloride is from 1:1:1 to 1:3:3, hydrolyzing the reaction product under acidic conditions, and recovering said hydroxyalkane diphosphonic compound.

Compounds of formula I can be produced by reacting 2-amino-isobutyric acid or proline (2-pyrrolidine carboxylic acid) with phosphorous acid and phosphorus trichloride, the molar ratio being 1:1:1 to 1:3:3 and hydrolyzing the reaction product under acid conditions. The phosphorous acid and phosphorus trichloride, incidentally, need not be present in the same molar ratio. The reaction occurs at a temperature of 50° C. to 140°

C., preferably in the temperature range of from 70° C. to 120° C.

In the reaction of 2-amino-isobutyric acid with phosphorous acid and phosphorus trichloride, it has proved to be particularly appropriate to carry out the reaction of said substances in the molar ratio 1:1.5:1.5. If, on the other hand, one uses as starting substance, proline (2-pyrrolidine carboxylic acid), it is advantageous to select the molar ratio to phosphorous acid and to phosphorus trichloride in the range of 1:2:2.

It is further expedient, although not necessary, to carry out the reaction in the presence of inert organic solvents such as chlorinated hydrocarbons, for example chlorobenzene or tetrachloroethane, or cyclic ethers, for example dioxane. A practical procedure is first to mix the solvent with the aminocarboxylic acid and the phosphorous acid and to heat the mixture to a temperature of preferably 70° C. to 120° C., then, in this order, to slowly add phosphorus trichloride. The batch is then left at this elevated temperature for a while. Thereafter the acid hydrolysis takes place by addition of an aqueous acid.

However, it is not necessary to add an acid, but it suffices to add a corresponding quantity of water to the acid mixture. The hydrolysate is processed according to known methods, in that, for example, following a filtration, the aqueous phase is separated, and possibly after concentration, the hydroxy-diphosphonic acid is precipitated by addition of suitable solvents such as acetone or acetone-alcohol mixtures.

A further possible expedient is to conduct the reaction between the 2-amino-isobutyric acid or proline and the phosphorous acid and phosphorus trichloride by mixing an excess of phosphorous trichloride of over 3 mols with the amino acid, optionally in the presence of an inert organic solvent, and adding sufficient water thereto to convert the excess of the phosphorus trichloride to the desired ratio of phosphorous acid.

The new hydroxyalkane diphosphonic acids can be transformed into the corresponding non-toxic, pharmacologically acceptable, water-soluble salts by complete or partial neutralization with inorganic, organic or quaternary bases, such as alkali metal hydroxide, for example NaOH, KOH, LiOH; alkali metal carbonates, such as $Na_2CO_3$; $NH_4OH$; lower alkylamines, such as methylamine; lower alkanolamines, such as monoethanolamine, diethanolamine, triethanolamine; and tetra-lower-alkyl-ammonium hydroxides, such as tetra-methylammonium hydroxide.

The new hydroxyalkane diphosphonic acids, including their alkali metal, ammonium, or alkanolamine salts, are good complex formers for alkaline earth ions, preferably calcium ions, and therefore can find use especially for processes of water softening. It is unnecessary to operate with stoichiometric quantities, and also with the use of substoichiometric quantities, possibly even with quantities of 0.2 to 5 mg/l, calcite precipitations can be delayed considerably.

Thus, the compounds of the invention are eminently suitable as anti-corrosion and anti-scaling agents for cooling water, particularly combined with known additives, such as bivalent zinc and/or cadmium salts, orthophosphates, chromates or hydrazine hydrate.

The amount which is to be regarded as stoichiometric according to the compound which is used can be readily determined by a simple test. Theoretically, 1 mol of the compound should sequester up to 2 mols of calcium ions. In general, the complex formers are used in quantities of from 1 mol per 2,000 mols of metal ions up to six times the stoichiometric quantity.

Owing to the said properties, the new complex formers can also be used, for example, for the descaling of fabrics in which alkali earth salts have been deposited, and to reduce the ash concentration in fabrics. Furthermore, they are suitable for processes for cleaning rigid articles such as metal or glass. Their use as additive to bottle-rinsing agents is particularly important.

Advantageously, the complex forming capacity can also be used in systems in which copper ions have an undesirable influence. Examples of this which may be mentioned are the avoidance of the decomposition of percompounds or, alternatively, the stabilization of fats and soaps. Furthermore, the said compounds are suitable for use as additives to dyeing baths for textiles in order to bind, in a complex manner, those metal ions which form undesirable tints.

Finally, the complex forming capacity can also be used to feed so-called trace elements to plants. The satisfactory complex forming capacity of these compounds is also exhibited by the fact that the known red color, which is otherwise observed when adding rhodanide to solutions which contain tervalent iron, does not occur. Thus, these properties can also be used in an advantageous manner in order to prevent the depositing of iron compounds, particularly iron hydroxide, on fabrics or when washing bottles. The new compounds can also be used in galvanic baths instead of cyanides.

Finally, they are also suitable as builder substances with complexing properties in washing and cleaning agents and can be used in combination with known anionic, cationic or non-ionic, surface-active compounds. Furthermore, they can be used in combination with caustic alkalies, alkali metal carbonates, alkali metal silicates, alkali metal phosphonates, or alkali metal borates.

The diphosphonic acids which have been described are also suitable as active substances in pharmaceutical or cosmetic preparations which are used for the therapeutic or prophylactic treatment of disorders in the calcium or phosphate metabolism and the associated diseases. These diseases can be divided into two categories:

1. Abnormal depositions of difficulty soluble calcium salts, mostly calcium phosphate, cause bone malformations, pathological hardening of tissues and secretions in organs.

2. The abnormal dissolution of hard tissues causes losses of hard bone substance, which cannot be replaced or are replaced only by incompletely crystallized tissue. This dissolution is frequently accompanied by pathologically high calcium and phosphate concentrations in the plasma.

These diseases include: osteoporosis, osteodystrophy, Paget's disease, myositis ossificans, Bechterew's disease, cholelithiasis, nephrolithiasis, urinary calculus, hardening of the arteries (sclerosis), arthritis, bursitis, neuritis, tetany.

Instead of the free acids, their non-toxic pharmacologically acceptable salts, such as sodium, potassium, magnesium, ammonium and substituted ammonium salts, such as mono-, di or triethanol ammonium salts, are suitable for pharmaceutical use. The partial salts, in which only a portion of the acid protons is replaced by other cations, can be used as well as full salts, although partial salts, which react substantially neutral in aqueous solution (pH 5 to 9) are preferred. Mixtures of the aforesaid salts may also be used.

The dosage of the compounds used is variable and depends upon the prevailing conditions, such as the nature and the seriousness of the disease, the duration of the treatment and the particular compound. Individual doses can be from 0.05 to 500 mg per kg of body weight. The preferred dosage is 1 to 50 mg per kg of body weight per day and can be administered in up to four doses daily. Owing to the limited resorption, the higher dosages are required in the case of oral application. In the case of treatment over a long period of time, smaller doses are necessary after high initial doses in order to maintain the desired effect.

Doses of less than 0.05 mg/kg of body weight do not have any significant effect upon the pathological calcification or the resolution of calcified tissues. Long-term toxic side effects can occur in the case of doses in excess of 500 mg/kg of body weight. The described diphosphonic acids or their salts may be administered orally in the form of tablets or capsules, as well as subcutaneously, intramuscularly or intravenously in hypertonic solution. The preferred dosage ranges for these uses are (in mg/kg per day):
Orally: 1.0 to 50.0
Subcutaneously: 1.0 to 10.0
Intramuscularly: 0.05 to 10.0
Intravenously: 0.05 to 2.0

The substances can be formulated for administration in the form of tablets, pills, capsules or injection solutions.

They can be used in combination with the hormone calcitonine for the treatment of disorders of calcium or phosphate metabolism. Suitable calcitonines are synthetic and natural calcitonine obtained from pigs, cattle and salmon. It is also possible to use calcitonines whose biological efficacy has been changed by the substitution of individual amino acid groups in the peptide chain of the natural calcitonines which comprise 32 amino acids. Some of these calcitonines which have been mentioned are commercially available.

In the case of animals, the substances can also be used in fodder and as fodder additives.

When used in cosmetic preparations, such as mouthwashes and toothpastes, the diphosphonic acids in accordance with the invention or their pharmacologically harmless salts in concentrations of 0.01% to 5% by weight, prevent the formation of tartar or plaque.

Finally, the new diphosphonic acids are also suitable as an additive to preparations for producing $99^m$ technetium radio diagnostics. Diseases of the bones and tissues can be recognized and localized by radiography. The isotope technetium $99^m$, which has a half-life period of six hours, has been used for this purpose in recent times.

Convenient devices are available for its production, from which the radioactive isotope in the form of $99^m$ pertechnetate can be obtained by elution with an isotonic solution of common salt.

Pertechnetate $99^m$ differs from the radioactive fluorine or strontium previously used in that it does not combine specifically in the skeleton or in calciferous tumors in the body. It has to be reduced to a low oxidation stage for use and then has to be stabilized in this oxidation stage by means of a suitable complex former. Furthermore, the complex former must have a high selectivity for the preferred absorption by the skeleton or by calciferous tumors.

It has been discovered that the complexing diphosphonic acids described above, or pharmaceutically harmless water-soluble salts thereof, are particularly suitable for these purposes. The phosphonic acids are used together with a pharmaceutically acceptable tin (II), chromium (II) or iron (II) salt, the reducing salts being present in stoichiometric subordinate quantities relative to the phosphonic acids or water-soluble salts thereof. Thus, it is possible to produce, in a simple manner, a highly stable product which is suitable for sale in a solid form as tablets or in the form of a solution contained in an ampoule.

After the diphosphonic acid/reduced metal salt preparation has been added to a pertechnetate solution, the resultant complex forms a very effective means for diagnosing bone tumors, local disorders in bone metabolism and calciferous tissue tumors.

The present invention will now be further described by means of the following examples, which are not limitative in any manner.

EXAMPLE 1

1-Hydroxy-2-amino-2-methylpropane-1,1-diphosphonic acid 0.48 mol of 2-amino-isobutyric acid and 0.72 mol of $H_3PO_3$ in 250 ml of chlorobenzene were heated to 100° C., then slowly 0.72 mol of $PCl_3$ was added in drops. After post heating for three hours, the reaction mixture was hydrolyzed with an excess of water (240 ml). The aqueous phase was separated from the chlorobenzene and filtered through activated carbon. The water-clear hydrolysate was concentrated to 180 ml, precipitated with 8 times the volume of acetone, and dried.

| Analyses: | | | | |
|---|---|---|---|---|
| Calculated: | C 19.32% | H 5.03% | P 24.90% | N 5.62% |
| Found: | 19.28% | 5.22% | 24.90% | 5.63% |

| Molecular weight: | |
|---|---|
| Calculated: | 249.9 |
| Found: | 249.0 |
| m.p.: | 217° C. |

By $^1$H-NMR and $^{31}$P-NMR spectroscopy, the structure

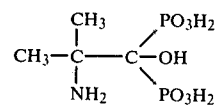

was confirmed.

EXAMPLE 2

To a mixture of 1 mol of 2-amino-isobutyric acid, 600 ml of chlorobenzene and 4 mols of $PCl_3$, there were added 6 mols of water at room temperature. Then the reaction mixture was heated for 5 hours at 100° C. Thereafter, the reaction product was hydrolyzed with 500 ml $H_2O$. The solvent was separated and the batch processed analogously to Example 1.

EXAMPLE 3

2'-Pyrrolidine-1-hydroxymethane-1,1-diphosphonic acid 0.43 mol of proline and 0.86 mol of $H_3PO_3$ in 250 ml dioxane were heated to 80° C. and admixed with 0.86 mol of $PCl_3$. The reaction mixture was left at this temperature for 20 hours, then hydrolyzed with 500 ml water and filtered through activated carbon. The diphosphonic acid which precipitated during concentration of the filtrate, was separated and dried at 60° C. under vacuum. The compound was present as a monohydrate and was chromatographically pure.

Analyses:

| Calculated: | C 21.75% | H 5.19% | P 22.17% | N 5.02% |
|---|---|---|---|---|
| Found: | 21.50% | 5.42% | 22.20% | 5.02% |

| Molecular weight: | |
|---|---|
| Calculated: | 278 |
| Found: | 279.1 |
| m.p.: | 195° C. (decomp.) |

Through $^1$H-NMR and $^{31}$P-NMR measurements, the structure below was confirmed:

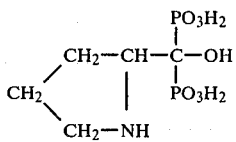

EXAMPLE 4

In the following table, the threshold activity of the new compounds is given in comparison with known 3-aminoalkane-1,1-diphosphonic acids. The hardness stabilizing effect was determined as follows:

Solutions having a water hardness of 20° d.H. (4/5 Ca and 1/5 Mg hardness) and an additional content of 4.5 gm/l of $Na_2CO_3$, 0.6 gm/l of sodium silicate ($SiO_2$:-$Na_2O$ ratio=3.36) and 150 mg/l of the inhibitor stated below, were heated for 30 minutes to 95° C. Then the proportion of calcium remaining in the solution was determined by flame photometry.

The results are given in Table I.

TABLE I

| No. | Substance | % CaO in Solution |
|---|---|---|
| (1) | 1-Hydroxy-2-amino-2-methyl-propane-1,1-diphosphonic acid | 94.3 |
| (2) | 2'-Pyrrolidine-1-hydroxymethane-1,1-diphosphonic acid | 75.8 |
| | 1,3-Diamino-propane-1,1-diphosphonic acid | 50.2 |
| | 3-amino-1-hydroxypropane-1,1-diphosphonic acid | 35.7 |

EXAMPLE 5

Pharmaceutical Preparations

For the production of pharmaceutical preparations in the form of a tablet, the known methods of preparation were followed to produce a tablet having an effective dosage unit composition as follows:

Compound of Example 1: 100 mgm
Lactose: 100 mgm
Starch: 47 mgm
Magnesium stearate: 3 mgm For the production of pharmaceutical preparations in the form of a capsule, the known methods of preparation are followed to produce a capsule having an effective dosage unit composition as follows:

Compound of Example 3: 100 mgm
Starch: 20 mgm
Sodium lauryl sulfate: 1 mgm

The compounds of the invention are interchangeable in the above formulations. In another series of compositions, the free acids in the above formulations were replaced by the corresponding amounts of the tetrasodium or trisodium salts of the acids, respectively.

EXAMPLE 6

Cosmetic Preparations

The following recipes are suitable as a basic formula for toothpastes:

| | | Parts by Weight |
|---|---|---|
| (a) | Glycerin | 60.0 |
| | Water | 13.5 |
| | Sodium carboxymethyl-cellulose | 0.6 |
| | Silicic acid zerogel | 20.0 |
| | Sodium laurylsulfate | 2.0 |
| | Essential oils | 1.0 |
| | Sweetening agent | 0.4 |
| | Compound of Example 3 | 2.5 |
| (b) | Glycerin | 30.0 |
| | Water | 18.5 |
| | Sodium carboxymethyl-cellulose | 1.0 |
| | Aluminum hydroxide | 44.0 |
| | Sodium laurylsulfate | 1.0 |
| | Pyrogenic silicic acid | 1.5 |
| | Essential oils | 1.5 |
| | Sweetening agent | 0.5 |
| | Compound of Example 1 | 2.0 |

Suitable as a basic formulation for mouthwashes is the following recipe:

| | Parts by Weight |
|---|---|
| Ethyl alcohol | 19.5 |
| Glycerin | 7.5 |
| Water | 70.0 |
| Essential oils | 0.2 |
| Sodium laurylsulfate | 0.1 |
| Antiseptic (chlorothymol) | 0.1 |
| Sweetening agent | 0.1 |
| Compound of Example 3 | 2.5 |

The corresponding neutral salts such as the sodium salts can also be employed.

By regular use of the mouthwashes and/or toothpastes containing the above-mentioned hydroxyalkane dicarboxylic acids, according to the invention, the formation of tartar could be considerably reduced. The formation of hard compact plaque on the teeth was to a great extent prevented.

The preceding specific embodiments are illustrative of the practice of the invention. It is to be understood, however, that other expedients known to those skilled in the art or discussed herein may be employed without departing from the spirit of the invention or the scope of the appended claims.

We claim:

1. An hydroxyalkane diphosphonic compound selected from the group consisting of (A) acids having the formula $$X-\underset{PO_3H_2}{\overset{PO_3H_2}{\underset{|}{C}}}-OH$$

wherein X is a member selected from the group consisting of

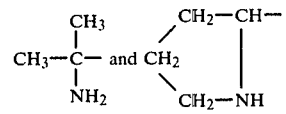

and (B) a non-toxic pharmacologically-acceptable water-soluble salt thereof.

2. The hydroxyalkane diphosphonic compound of claim 1 being a compound selected from the group consisting of (A) 1-hydroxy-2-amino-2-methylpropane-1,1-diphosphonic acid and (B) a non-toxic, pharmacologically-acceptable, water-soluble salt thereof.

3. The hydroxyalkane diphosphonic compound of claim 1 being a compound selected from the group consisting of (A) 2'-pyrrolidine-1-hydroxymethane-1,1-diphosphonic acid and (B) a non-toxic, pharmacologically-acceptable, water-soluble salt thereof.

* * * * *